United States Patent
Cornish et al.

[11] Patent Number: 6,132,389
[45] Date of Patent: Oct. 17, 2000

[54] PROXIMALLY TAPERED GUIDEWIRE TIP COIL

[75] Inventors: Wayne E. Cornish, Oceanside; Lawrence E. Brennan, Temecula; David M. Anderson, Oceanside; Marc M. Jalisi, Temecula, all of Calif.

[73] Assignee: Advanced Cardiovascular Systems, Inc., Santa Clara, Calif.

[21] Appl. No.: 09/065,646

[22] Filed: Apr. 23, 1998

[51] Int. Cl.[7] ............................................ A61B 5/00
[52] U.S. Cl. ............................ 600/585; 604/95; 604/96; 604/280
[58] Field of Search ......................... 600/585, 433, 600/434; 604/95, 96, 280, 281, 282

[56] References Cited

U.S. PATENT DOCUMENTS

| | | | |
|---|---|---|---|
| 4,538,622 | 9/1985 | Samson et al. | 128/772 |
| 4,748,986 | 6/1988 | Morrison et al. | 128/772 |
| 4,832,047 | 5/1989 | Sepetka et al. | 600/585 |
| 5,059,183 | 10/1991 | Semrad | 604/158 |
| 5,061,273 | 10/1991 | Yock | 606/194 |
| 5,120,308 | 6/1992 | Hess | 600/585 |
| 5,135,503 | 8/1992 | Abrams | 604/164 |
| 5,267,574 | 12/1993 | Viera et al. | 128/772 |
| 5,341,818 | 8/1994 | Abrams et al. | 128/772 |
| 5,345,945 | 9/1994 | Hodgson et al. | 128/772 |
| 5,497,785 | 3/1996 | Viera | 128/772 |
| 5,516,336 | 5/1996 | McInnes | 606/194 |
| 5,606,979 | 3/1997 | Hodgson | 128/772 |
| 5,640,970 | 6/1997 | Arenas | 128/772 |
| 5,769,796 | 6/1998 | Palermo | 600/585 |
| 5,830,155 | 11/1998 | Frechette et al. | 600/585 |
| 5,836,892 | 11/1998 | Lorenzo | 600/585 |

*Primary Examiner*—Cary O'Connor
*Assistant Examiner*—Pamela Wingood
*Attorney, Agent, or Firm*—Heller Ehrman White & McAuliffe

[57] ABSTRACT

The disclosure is directed to a guidewire having an elongate core member with at least one distally tapered portion at the distal section, with a flexible body member disposed around said distal section. The flexible body member is preferably comprised of a metallic helical coil that has proximally tapered portion at the proximal end, with a diameter similar to the outer diameter of the elongate core member at the point of attachment thereto. The distal end of the flexible body member is attached to the distal end of the elongate core member. The proximal taper of the flexible body member provides a smooth transition from the elongate core member to the flexible body member while minimizing the amount of bonding material needed and the resulting localized stiff portion at the point of connection between the proximal end of the flexible body member and the elongate body member.

10 Claims, 2 Drawing Sheets

PROXIMALLY TAPERED GUIDEWIRE TIP COIL

BACKGROUND

This invention relates to the field of guidewires for advancing intraluminal devices such as stent delivery catheters, balloon dilatation catheters, atherectomy catheters and the like within body lumens.

In a typical coronary procedure a guiding catheter having a preformed distal tip is percutaneously introduced into a patient's peripheral artery, e.g. femoral or brachial artery, by means of a conventional Seldinger technique and advanced therein until the distal tip of the guiding catheter is seated in the ostium of a desired coronary artery. There are two basic techniques for advancing a guidewire into the desired location within the patient's coronary anatomy, the first is a pre-load technique which is used primarily for over-the-wire (OTW) devices and the bare wire technique which is used primarily for rail type systems.

With the pre-load technique, a guidewire is positioned within an inner lumen of an OTW device such as a dilatation catheter or stent delivery catheter with the distal tip of the guidewire just proximal to the distal tip of the catheter and then both are advanced through the guiding catheter to the distal end thereof. The guidewire is first advanced out of the distal end of the guiding catheter into the patient's coronary vasculature until the distal end of the guidewire crosses the arterial location where the interventional procedure is to be performed, e.g. a lesion to be dilated or a dilated region where a stent is to be deployed. The catheter, which is slidably mounted onto the guidewire, is advanced out of the guiding catheter into the patient's coronary anatomy by sliding over the previously introduced guidewire until the operative portion of the intravascular device, e.g. the balloon of a dilatation or a stent delivery catheter, is properly positioned across the arterial location.

Once the catheter is in position with the operative means located within the desired arterial location, the interventional procedure is performed. The catheter can then be removed from the patient by sliding it back over the guidewire. Usually, the guidewire is left in place for a period of time after the procedure is completed to ensure re-access to the arterial location if it is necessary. For example, in the event of arterial blockage due to dissected lining collapse, a rapid exchange type perfusion balloon catheter such as described and claimed in U.S. Pat. No. 5,516,336 (McInnes et al), can be advanced over the in-place guidewire so that the balloon can be inflated to open up the arterial passageway and allow blood to perfuse through the distal section of the catheter to a distal location until the dissection is reattached to the arterial wall by natural healing.

With the bare wire technique, the guidewire is first advanced by itself through the guiding catheter until the distal tip of the guidewire extends beyond the arterial location where the procedure is to be performed. Then a rail type catheter, such as described in U.S. Pat. No. 5,061,395 (Yock) and the previously discussed McInnes et al. which are incorporated herein by reference, is mounted onto the proximal portion of the guidewire which extends out of the proximal end of the guiding catheter which is outside of the patient. The catheter is advanced over the guidewire, while the position of the guidewire is fixed, until the operative means on the rail type catheter is disposed within the arterial location where the procedure is to be performed. After the procedure the intravascular device may be withdrawn from the patient over the guidewire or the guidewire repositioned within the coronary anatomy for an additional procedure.

Further details of guidewires, and devices associated therewith for various interventional procedures can be found in U.S. Pat. No. 4,748,986 (Morrison et al.); U.S. Pat. No. 4,538,622 (Samson et al.): U.S. Pat. No. 5,135,503 (Abrams); U.S. Pat. No. 5,341,818 (Abrams et al.); and U.S. Pat. No. 5,345,945 (Hodgson, et al.) which are hereby incorporated herein in their entirety by reference thereto.

Conventional guidewires for angioplasty, stent delivery, atherectomy and other vascular procedures usually comprise an elongate core member with one or more tapered sections near the distal end thereof and a flexible body member such as a helical coil or a tubular body of polymeric material disposed about the distal portion of the core member. A shapable member, which may be the distal extremity of the core member or a separate shapeable ribbon which is secured to the distal extremity of the core member extends through the flexible body and is secured to the distal end of the flexible body by soldering, brazing or welding which forms a rounded distal tip. Torquing means are provided on the proximal end of the core member to rotate, and thereby steer, the guidewire while it is being advanced through a patient's vascular system. The leading tip is highly flexible and will not damage or perforate the vessel and the portion behind the distal tip is increasingly stiff which better supports a balloon catheter or similar device.

In an ordinary guidewire, the flexible body member is of constant diameter and is of greater diameter than the core member to which it is being attached. The attachment method normally comprises a welding, soldering or brazing process, or some other bonding process which might include the use of adhesives, or mechanical means. The solder, braze, or weld material is applied to the flexible body and the core in sufficient quantity to effect a solid joint between the two elements.

A problem inherent in this design is that the body of solder required to secure the helical coil at the bond disrupts the flexibility, i.e., there is a stiff spot which prevents a smooth transition. The present invention solves these and other problems.

SUMMARY

The present invention is directed to an improved guidewire which has a smooth transition at the bond of the proximal end of the flexible body to the core member. This allows for smoother bends in the guidewire and easier tracking and translation of devices that slide over the guidewire.

The guidewire of the present invention has an elongated core member which has a distal section and a proximal section. Preferably, the distal section of the core has at least one tapered portion that tapers in a reduced diameter towards the distal end of the device. A flexible body member, for example, a helical coil or polymeric tubular member, is disposed around at least part of the distal section of the elongate core.

In accordance with the present invention, the proximal end of the flexible body member is tapered in the proximal direction to more closely approximate the diameter of the core member to which it is attached in order to reduce the amount of bonding material necessary to form the joint, and to make for a smoother joint transition. These and other advantages of the invention will become more apparent from the following detailed description of the invention when taken in conjunction with the accompanying exemplary drawings.

DETAILED DESCRIPTION OF THE INVENTION

Figure 1:
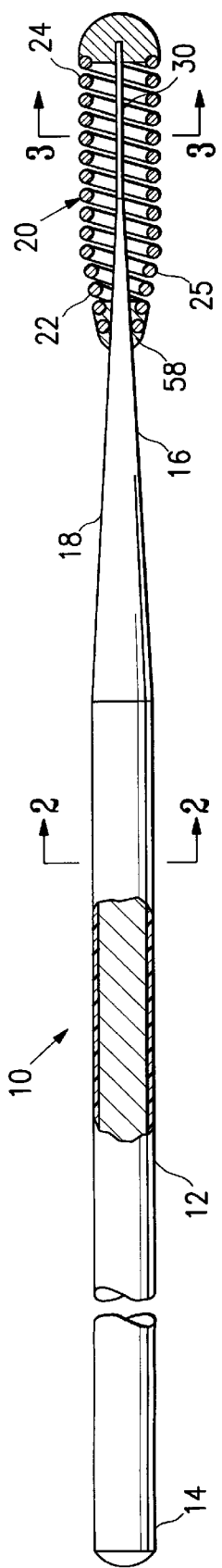
FIG. 1 is an elevational view partially in section of a guidewire embodying features of the invention.

FIG. 1 depicts a guidewire 10 which is an embodiment of the invention which has an elongate core member 12 with a proximal section 14 and a distal section 16. The distal section 16 of the elongate member has at least one distally tapered portion 18. A flexible body member 20 is disposed around the distal section. The flexible body member 20, which has a proximal end 22 and a distal end 24, and which has a proximally tapered section 25 is attached to the elongate core member at both its proximal end 22 and distal end 24. Preferably, the proximally tapered section 25 of the flexible body member is configured to have an inner diameter similar to the outer diameter of the elongate core member at the point of attachment of the proximal end of flexible body member.

Figure 3:
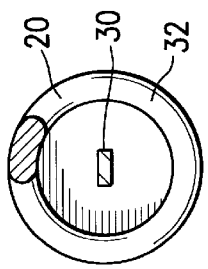
FIG. 3 is a cross sectional view of the guidewire of FIG. 1 taken along lines 3—3.
Figure 2:
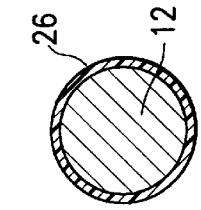
FIG. 2 is a cross sectional view of the guidewire of FIG. 1 taken along the lines 2—2.

FIG. 2 is a cross sectional view of the guidewire of FIG. 1 taken at section 2—2, and shows a substantially circular cross section of the elongate core member 12, and a layer of lubricious coating 26. FIG. 3 shows a cross sectional view of the guidewire of FIG. 1 taken at section 3—3, and depicts the flexible body member 20 and a flattened distal end of the elongate core member 30 disposed within the flexible body member 20.

The elongate core member 12 is typically comprised of metal, preferably stainless steel or a nickel titanium alloy or a combination thereof, but can also consist of any material that yields the approximate mechanical properties of the named metals so long as the material is sufficiently biocompatible. Other materials such as high strength alloys, may also be used for the core member, either alone, or in combination with other materials such as those previously mentioned. The proximal section of the core member 14 and any portion of the core member not covered by the flexible body member 20 may optionally be used with a lubricious coating 26 such as a flouropolymer, eg. TEFLON® by DuPont. It may also be coated with a silicone based coating, such as MICROGLIDE™ coating used by the present assignee, Advanced Cardiovascular Systems, Inc. on many of its commercially available guidewires. Other similar coatings, for example, hydrophylic coatings, or a combination of any of the above mentioned coatings may also be used.

The core member 12 preferably has a substantially circular cross section throughout its length, save the distal end which optionally may be flattened into a ribbon 30 having a generally rectangular shaped transverse cross section to facilitate manual shaping by the guidewire user.

The distal section 16 of the elongate core can be from about 0.39 inches (1 cm) to about 11.8 inches (30 cm), preferably about 0.79 inches (2 cm) to about 5.9 inches (15 cm) and has at least one tapered portion 18, tapered distally. In FIG. 1, the distal section of the elongate core 16 has one distally tapered portion 18 leading to the distal end of the elongate core 30 which may or may not be flattened. The distally tapered portion 18 of the distal section can be from about 0.39 inches (0.5 cm) to about 5.9 inches (15 cm) in length, preferably about 0.79 inches (2 cm) to about 3.9 inches (10 cm) in length, and most preferably about 2.3 inches (6 cm) to about 3.1 inches (8 cm) in length. The angle of the distally tapered portion 18 can be from about 0.1° to 10°, preferably about 0.1 to 3° and most preferably about 0.11 to 0.15°.

The distally tapered portion or portions 18 of the distal section 16 of the elongate core member are preferably formed in the elongate core by centerless grinding but they may be made in a variety of ways, including hammer forging, chemical etching, laser machining or casting.

The diameter of the proximal section 14 of the elongate core is about 0.01 inches (0.25 mm) to about 0.045 inches (1.1 mm), preferably about 0.012 inches (0.30 mm) to about 0.018 inches (0.46 mm), and most preferably about 0.013 inches (0.33 mm) to about 0.015 inches (0.38 mm). The distal end 30 of the elongate core, which may or may not be flattened, has a cross sectional diameter of about 0.001 inches (0.025 mm) to about 0.006 inches (0.15 mm), preferably about 0.0015 inches (0.038 mm) to about 0.003 inches (0.076). The length of the elongate core member 12 as a whole is about 35 inches (90 cm) to about 118 inches (300 cm), preferably about 59 inches (150 cm) to about 89 inches (225 cm), and most preferably about 75 inches (190 cm).

The flexible body member 20 is disposed around all or part of the distal section 16 of the elongate core member, and has a distal end 24 and a proximal end 22. The flexible body member 20 can be comprised of many suitable materials that allow for increasing the diameter of the guidewire in the distal section without adding substantial stiffness to that section. Suitable materials include polymers, composites, and metals. Preferably the flexible body member 20 is comprised of a helical shaped metallic coil, more preferably a metal or composition of metal or alloys with some degree of radiopacity in order to facilitate flouroscopic viewing of the device while in use. Metals suitable for the flexible body member 20 may include gold, platinum, tantalum, stainless steel, and nickel titanium alloys, MP35N, or a combination or alloy of any of the foregoing. A flexible body member 20 comprised of metallic helical coils is typically comprised of coil winding material 32 that can have a cross sectional diameter of about 0.001 inches (0.025 mm) to about 0.008 inches (0.20 mm), preferably about 0.002 inches (0.05 mm) to about 0.004 inches (0.1 mm).

As shown in FIG. 1, the flexible body member 20 of the presently preferred invention has a proximally tapered section 25, ending in a proximal end 22 with an inner diameter similar to the outer diameter of the elongate core member at the point of proximal connection between the two. Such a configuration allows the two members to be connected with a minimum amount of bonding material at the proximal connection, which makes for a smoother and more continuous transition, and avoids stiff spots in the guidewire resulting from an accumulation of solder or other bonding material at the bonding site.

The proximally tapered portion 25 of the flexible body member provides for a smoother transition from the elongate core member 12 to the flexible body member 20. The smoother transition allows the devices which are guided by the guidewire device to track more easily over the guidewire.

Figure 4:
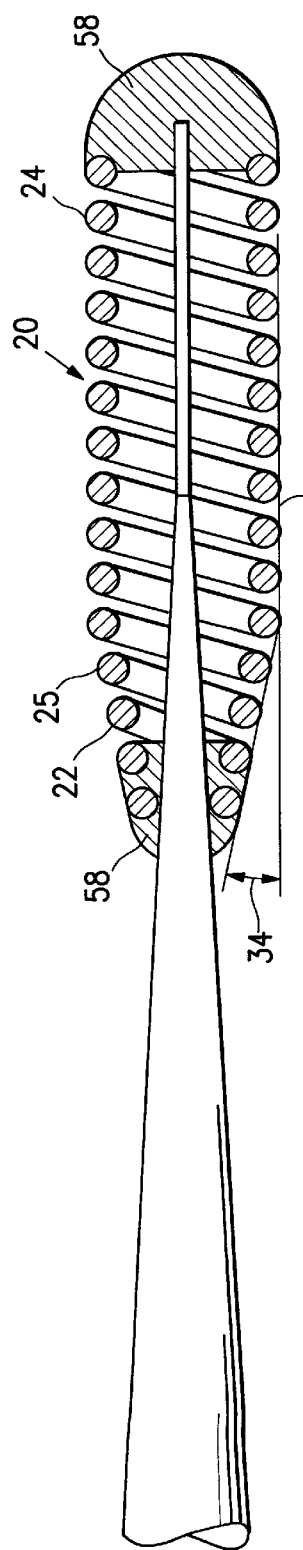
FIG. 4 is an enlarged view of the distal portion of the guidewire shown in FIG. 1.

FIG. 4 shows an enlarged view in partial section of a part of the distal section 16 of the guidewire 10 of FIG. 1. The flexible body member 20 is typically attached to the elongate core member 12 at its distal end 24 and its proximal end 22 by a suitable means such as soldering, brazing, or welding. Alternately, an adhesive bond using epoxy or cyanoacrylate could be used. The bonding material 58 can serve to further smooth the transition from the elongate core to the flexible body member.

The taper angle 34 of the proximally tapered section 25 of the flexible body member is the angle the tangent to the tapered section makes with the longitudinal axis of the flexible body member, can be from about 0.1 to 10°, preferably about 0.5 to 2°. The flexible body member 20 normally has a distal segment of substantially constant outer diameter 36, however, the proximally tapered section 25 of the flexible body member can extend over the entire length of the flexible body member 20. The distal end 24 of the flexible body member typically has an outer diameter approximately equal to the nominal outer diameter of the proximal section of the elongate core member and both diameters can vary with a maximum depending on the inner diameter of the lumen through which the guidewire must pass. Preferably, the nominal outer diameter of the flexible body member 20 is about 0.01 inches (0.25 mm) to about 0.05 inches (1.27 mm), more preferably about 0.012 inches (0.30 mm) to 0.018 inches (0.46 mm), and most preferably about 0.013 inches (0.33 mm) to about 0.015 inches (0.38).

Figure 5:
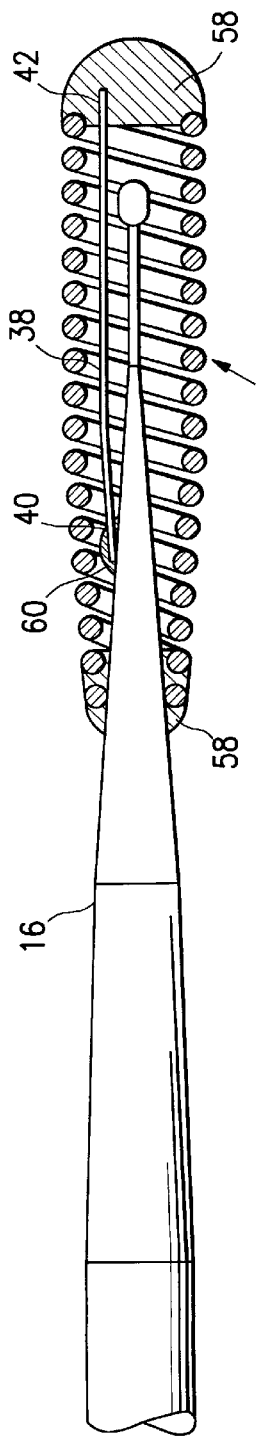
FIG. 5 is a partial elevational view of the distal section of an alternate embodiment of the invention which has a separate shaping ribbon extending from the distal extremity of the elongate core to the distal end of the coil.

FIG. 5 illustrates another embodiment of the invention similar to that depicted in FIG. 1 but further comprising a shapeable separate ribbon member 38 disposed between the distal section 16 of the elongate core member and the flexible body member 20. The shapeable ribbon member 38 has a proximal end 40 which is attached to the elongate core member 12 by a body of solder 60, and a distal end 42 which is attached to the distal end of the flexible body member 24 by a body of solder 58, and is typically comprised of flattened metallic wire, such as stainless steel, nickel titanium alloy or other suitable metal. The length of the shapeable ribbon member 38 can be about 0.039 inches (1 mm) to about 1.18 inches (30 mm), preferably about 0.39 inches (10 mm) to about 0.79 inches (20 mm). The cross section of the shapeable ribbon member 38 can be about 0.0005 inches (0.013 mm) by about 0.010 inches (0.25 mm), preferably about 0.001 inches (0.025 mm) by about 0.003 inches (0.075 mm).

Figure 6:
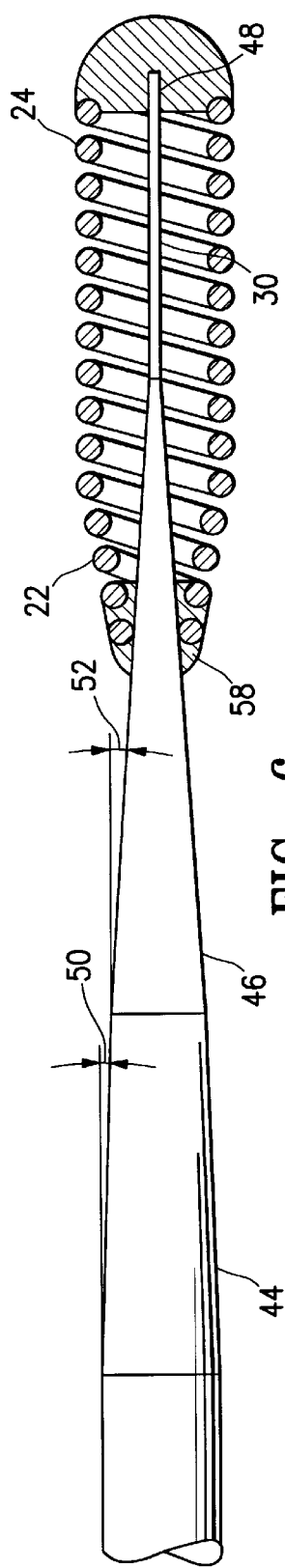
FIG. 6 is a partial elevational view of the distal section of an alternative embodiment of the invention which has two distal tapered segments in the elongate core member.

FIG. 6 depicts another embodiment of the invention wherein the distal section 16 of the elongate core member has a first tapered core segment 44 and a second tapered core segment 46. In this embodiment, the proximal end 22 of the flexible body member is attached to the elongate core member on the second tapered core segment 46 by a body of solder 58, but could also extend and be attached to the first tapered core segment 44. The distal end 24 of the flexible body member is attached to the elongate core member at its distal extremity 48.

The embodiment of FIG. 6 further comprises a first taper angle 50, which can be about 0.05° to about 10°, preferably about 0.1° to about 2°, and a second taper angle 52, which can be about 0.05° to about 10°, preferably about 0.2° to about 3°, with the second taper angle 52 preferably greater than the first taper angle 50. Though two tapered core segments are shown in FIG. 6, any number of tapered segments can be used, with the taper angle each tapered segment being greater than the taper angle of the tapered segment located immediately proximal to it.

The length of the first tapered core segment 44 can be about 0.39 inches (1 cm) to about 5.9 inches (15 cm), preferably about 1.18 inches (3 cm) to about 1.97 inches (5 cm). The length of the second tapered core segment 46 can be about 0.39 inches (1 cm) to about 5.9 inches (15 cm), preferably about 1.18 inches (3 cm) to about 1.97 inches (5 cm). Typically, the length of the second tapered core segment 46 is greater than the first. The flexible body member 20 of FIG. 6 is similar to that of FIG. 1, as are the distal end 30 and proximal section 14 of the elongate core member.

Figure 7:
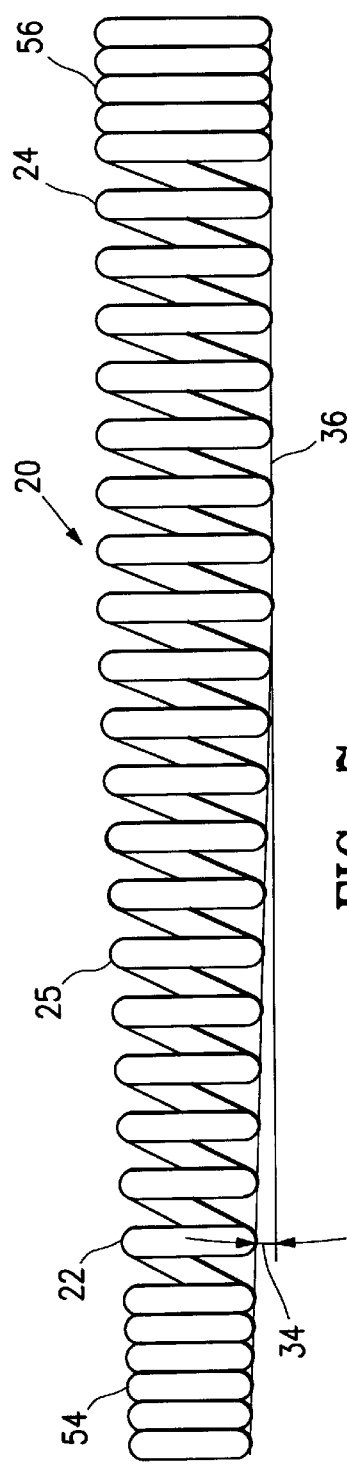
FIG. 7 is an elevational view of an embodiment of the flexible body element.

The device as shown in FIG. 7 is another embodiment of a flexible body member 20 having a proximal end 22 and a distal end 24 with a proximally tapered section 25. This embodiment of the flexible body member 20 is comprised of a helical coil. The proximally tapered section 25 is a gradual taper and terminates at the proximal end 22 in a proximal stack 54 wherein the coils of the body are wound closely together so as to touching or in close proximity to adjacent coils. A similar configuration exists at the distal end 24 where the distal end terminates in a distal stack 56. The purpose of the distal stack 56 and proximal stack 54 is to improve the joint of the coil 20 to the second tapered core segment 46. The length of the proximal stack 54 and distal stack 56 is from about 0.05 mm to about 1 mm. The coils of the flexible body member between the proximal stack 54 and the distal stack 56 are loosely wound with adjacent coils spaced from each other. The outer diameter of the distal end 24 of the flexible body member can be about 0.006" to about 0.05", preferably about 0.012" to about 0.016".

The taper angle 34 of the embodiment of the flexible body member shown in FIG. 7 is similar to that of the previous embodiments, as are the lengths of the proximally tapered section 25 and the distal segment of substantially constant diameter 36. The length of the flexible body member 20 can be about 0.39 inches (1 cm) to about 11.8 inches (30 cm), preferably about 1.97 inches (5 cm) to about 7.9 inches (20 cm). The proximally tapered section 25 of the flexibly body member can be about 0.039 inches (1 mm) to about 11.8 inches (300 mm), preferably about 0.2 inches (5 mm) to about 4 inches (100 mm). While particular forms of the invention have been illustrated and described, it will be apparent that various modifications can be made without departing from the spirit and scope of the invention. Accordingly, it is not intended that the invention be limited, except as by the appended claims.

What is claimed is:

1. A guidewire comprising:
    a) an elongate core member having a proximal section, a distal section, and a distal end;
    b) a flexible body member disposed about the elongate core member and having a distal end, a proximal end, and a proximally tapered section terminating at the proximal end which tapers proximally to a reduced inner diameter similar to an outside diameter of the distally tapered elongate core member adjacent to the proximal end of the flexible body member; and
    c) a body of bonding material disposed on the proximal end of the flexible body member securing the proximal end of the flexible body member to the elongate core member.

2. The guidewire of claim 1 wherein the distal end of the flexible body member is secured to the elongate core member.

3. The guidewire of claim 1 wherein the distal end of the flexible body member is attached to the distal end of the elongate core member.

4. The guidewire of claim 2 further comprising a shapeable ribbon member having a distal end and a proximal end with the proximal end thereof secured to the distal end of the elongate core member and the distal end of the shapeable ribbon attached to the distal end of the flexible body member.

5. The guidewire of claim 1 wherein the distal end of the elongate core member is flattened.

6. The guidewire of claim 1 wherein the flexible body member is comprised of a helical coil.

7. The guidewire of claim 6 wherein at least part of the helical coil is formed of a radiopaque material.

8. The guidewire of claim 1 wherein the distal section of the elongate core member further comprises a first tapered core segment having a first taper angle and a distally contiguous second tapered core segment having a second taper angle, with the first taper angle and the second taper angle having a value of up to 25° from a longitudinal axis of the elongated core member.

9. The guidewire of claim 8 wherein the second taper angle is greater than the first taper angle.

10. The guidewire of claim 9 wherein the second tapered core segment is longer than the first tapered core segment.

* * * * *